US012440839B2

(12) United States Patent
Belling et al.

(10) Patent No.: US 12,440,839 B2
(45) Date of Patent: Oct. 14, 2025

(54) HIGH-THROUGHPUT SYSTEM AND METHOD FOR THE TEMPORARY PERMEABILIZATION OF CELLS USING LIPID BILAYERS

(71) Applicants: THE REGENTS OF THE UNIVERSITY OF CALIFORNIA, Oakland, CA (US); NANYANG TECHNOLOGICAL UNIVERSITY, Singapore (SG)

(72) Inventors: Jason N. Belling, Los Angeles, CA (US); Steven J. Jonas, Los Angeles, CA (US); Joshua A. A. Jackman, Bradenton, FL (US); Nam-Joon Cho, Singapore (SG); Paul S. Weiss, Los Angeles, CA (US)

(73) Assignees: THE REGENTS OF THE UNIVERSITY OF CALIFORNIA, Oakland, CA (US); NANYANG TECHNOLOGICAL UNIVERSITY, Singapore (SG)

( * ) Notice: Subject to any disclaimer, the term of this patent is extended or adjusted under 35 U.S.C. 154(b) by 1275 days.

(21) Appl. No.: 17/269,985

(22) PCT Filed: Aug. 21, 2019

(86) PCT No.: PCT/US2019/047518
§ 371 (c)(1),
(2) Date: Feb. 19, 2021

(87) PCT Pub. No.: WO2020/041480
PCT Pub. Date: Feb. 27, 2020

(65) Prior Publication Data

US 2021/0346889 A1 Nov. 11, 2021

Related U.S. Application Data

(60) Provisional application No. 62/720,734, filed on Aug. 21, 2018.

(51) Int. Cl.
*B01L 3/00* (2006.01)
*C12N 15/90* (2006.01)

(52) U.S. Cl.
CPC ... *B01L 3/502761* (2013.01); *B01L 3/502715* (2013.01); *B01L 3/50273* (2013.01);
(Continued)

(58) Field of Classification Search
None
See application file for complete search history.

(56) References Cited

U.S. PATENT DOCUMENTS

| | | | |
|---|---|---|---|
| 8,211,712 | B2 | 7/2012 | Cho et al. |
| 10,427,124 | B2 | 10/2019 | Cho et al. |

(Continued)

FOREIGN PATENT DOCUMENTS

| | | |
|---|---|---|
| WO | WO 2013/059343 | 4/2013 |
| WO | WO 2017/040995 | 3/2017 |

(Continued)

OTHER PUBLICATIONS

Chen JY, Tsai WS, Shao HJ, Wu JC, Lai JM, Lu SH, Hung TF, Yang CT, Wu LC, Chen JS, Lee WH, Chang YC. Sensitive and Specific Biomimetic Lipid Coated Microfluidics to Isolate Viable Circulating Tumor Cells and Microemboli for Cancer Detection. PLoS One. Mar. 3, 2016 (Year: 2016).*

(Continued)

*Primary Examiner* — Lyle Alexander
*Assistant Examiner* — Mickey Huang
(74) *Attorney, Agent, or Firm* — VISTA IP LAW GROUP LLP

(57) ABSTRACT

A microfluidic device is disclosed that is used to process cells for the intracellular delivery of molecules or other cargo. The device includes one or more microchannels disposed in a substrate or chip and is fluidically coupled to
(Continued)

an inlet configured to receive a solution containing the cells and the molecules or other cargo to be delivered intracellularly to the cells. Each of the one or more microchannels has one or more constriction regions formed therein, wherein the inner surface(s) of the microchannels and the one or more constriction regions have a lipid bilayer disposed thereon. In some embodiments, multiple microfluidic devices operating in parallel are used to process large numbers of cells. The device and method have particularly applicability to delivering gene-editing molecules intracellularly to cells.

25 Claims, 8 Drawing Sheets

(52) U.S. Cl.
CPC .... *C12N 15/907* (2013.01); *B01L 2200/0647* (2013.01); *B01L 2300/16* (2013.01)

(56) References Cited

U.S. PATENT DOCUMENTS

| | | | | |
|---|---|---|---|---|
| 10,787,470 | B2 | 9/2020 | Cho et al. | |
| 2006/0014013 | A1 | 1/2006 | Saavedra et al. | |
| 2009/0191259 | A1 | 7/2009 | Li et al. | |
| 2009/0263670 | A1 | 10/2009 | Cho et al. | |
| 2013/0048499 | A1* | 2/2013 | Mayer | G01N 15/131 204/549 |
| 2014/0287509 | A1* | 9/2014 | Sharei | C12M 35/04 435/375 |
| 2016/0228839 | A1 | 8/2016 | Cho et al. | |
| 2016/0334395 | A1 | 11/2016 | Cho et al. | |
| 2017/0165667 | A1 | 6/2017 | Beaumont et al. | |
| 2019/0381507 | A1 | 12/2019 | Weiss et al. | |
| 2020/0040017 | A1 | 2/2020 | Cho et al. | |
| 2020/0347409 | A1 | 11/2020 | Weiss et al. | |
| 2021/0139825 | A1* | 5/2021 | Zahn | B01L 3/502761 |

FOREIGN PATENT DOCUMENTS

| | | | |
|---|---|---|---|
| WO | WO-2017040995 A1 * | 3/2017 | B01L 3/502715 |
| WO | WO 2018/039084 | 3/2018 | |
| WO | WO 2018/0399084 | 3/2018 | |

OTHER PUBLICATIONS

PCT International Search Report and Written Opinion for PCT/US2019/047518, Applicant: The Regents of the University of California, dated Nov. 15, 2019 (14 pages).
Guanying Chen, et al., Nanochemistry and Nanomedicine for Nanoparticle-based Diagnostics and Therapy, Chem. Rev. 2016, 116, 2826-2885; DOI: 10.1021/acs.chemrev.5b00148.
Xiaoyun Ding, et al., High-throughput nuclear delivery and rapid expression of DNA via mechanical and electrical cell-membrane disruption, Nature Biomedical Engineering, Mar. 2017, DOI: 10.1038/s41551-017-0039; https://www.researchgate.net/publication/314482988.
Jay T. Groves et al., Control of Cell Adhesion and Growth with Micropatterned Supported Lipid Membranes, Langmuir 2001, 17, 5129-5133, 48,1342.
Xin Han, et al., CRISPR-Cas9 delivery to hard-to-transfect cells via membrane deformation, Sci. Adv. 2015;1:e1500454; Aug. 14, 2015.
Kavoos Kolahdouzan, et al., Optimizing the Formation of Supported Lipid Bilayers from Bicellar Mixtures, Langmuir 2017, 33, 5052-5064, DOI: 10.1021/acs.langmuir.7b00210.
Isaac Ojea-Jimenez, et al., Engineered nonviral nanocarriers for intracellular gene delivery applications, Biomed. Mater. 7 (2012) 054106 (13pp), doi:10.1088/1748-6041/7/5/054106.
Fredrik Persson, et al., Lipid-Based Passivation in Nanofluidics, dx.doi.org/10.1021/nl204535h, Nano Lett. 2012, 12, 2260-2265.
Michael K. Riley II, et al., Recent Advances in Nanomaterials for Gene Delivery—A Review, Nanomaterials 2017, 7, 94; doi: 10.3390/nano7050094, www.mdpi.com/journal/nanomaterials.
Armon Sharei, et al., A vector-free microfluidic platform for intracellular delivery, 2082-2087, PNAS, Feb. 5, 2013, vol. 110, No. 6, www.pnas.org/cgi/doi/10.1073/pnas.1218705110.
Tinglu Yang, et al., Fabrication of Phospholipid Bilayer-Coated Microchannels for On-Chip Immunoassays, Anal. Chem. 2001, 73, 165-169.
Hao Yin, et al., Therapeutic genome editing by combined viral and non-viral delivery of CRISPR system components in vivo, Nat Biotechnol. Mar. 2016 ; 34(3): 328-333. doi:10.1038/nbt.3471.
Saziye Yorulmaz, et al., Influence of membrane surface charge on adsorption of complementproteins onto supported lipid bilayers, Colloids and Surfaces B: Biointerfaces 148 (2016) 270-277.
PCT International Preliminary Report on Patentability (Chapter I of the Patent Cooperation Treaty) for PCT/US2019/047518, Applicant: The Regents of the University of California, Form PCT/IB/326 and 373, dated Mar. 4, 2021 (12 pages).

* cited by examiner

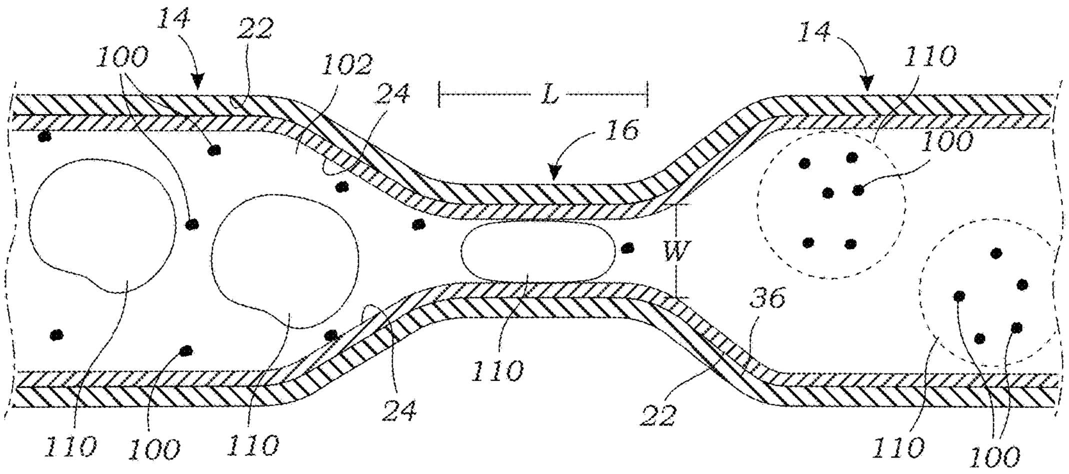
FIG. 4
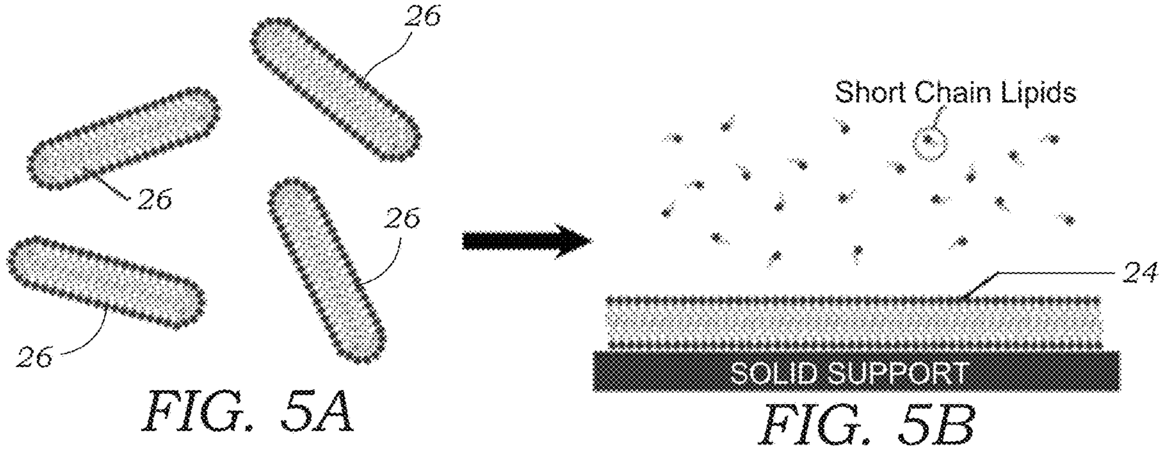
FIG. 5A
FIG. 5B
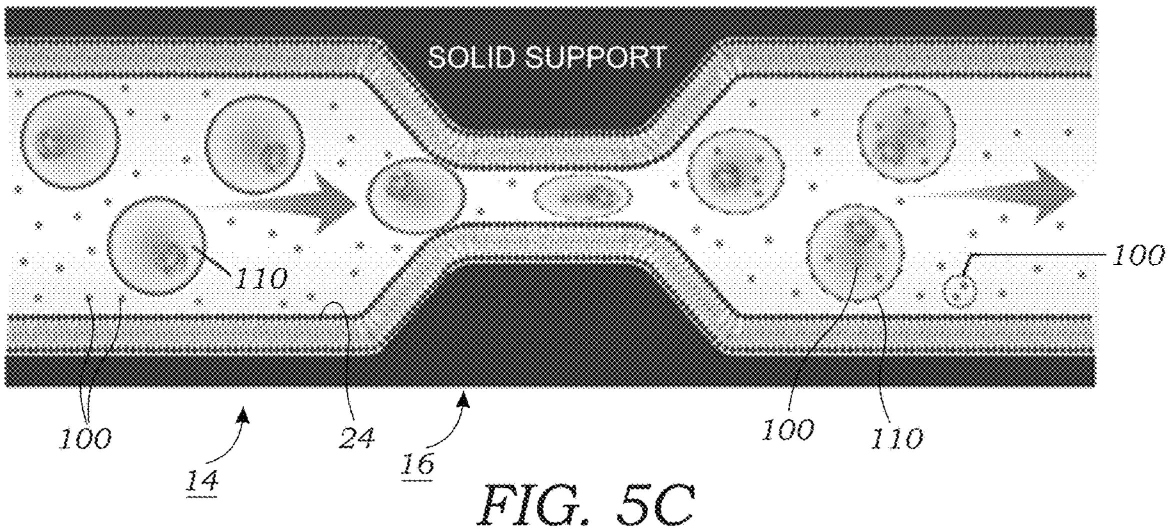
FIG. 5C

FIG. 8B
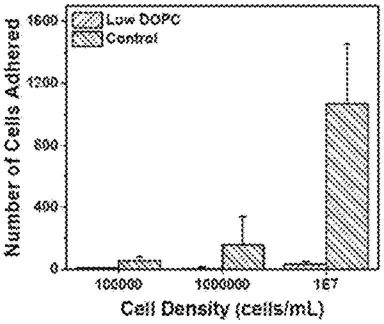
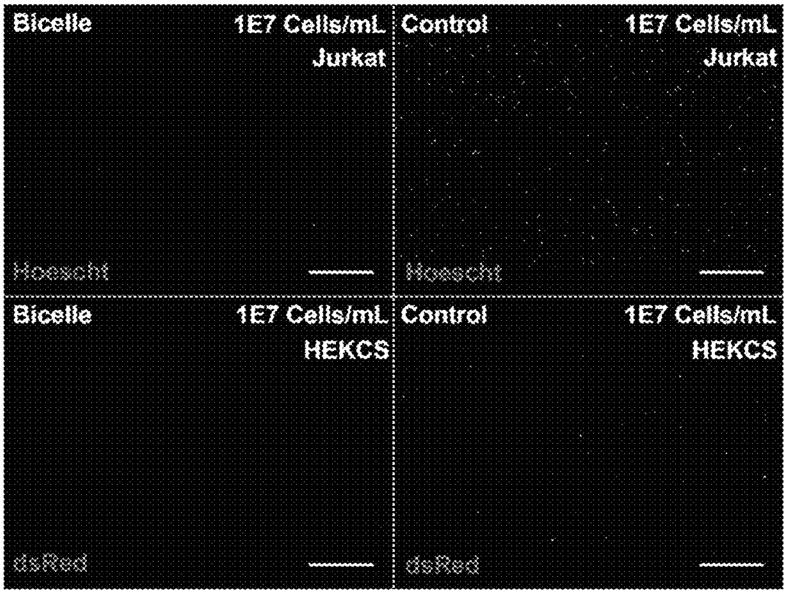
FIG. 8A
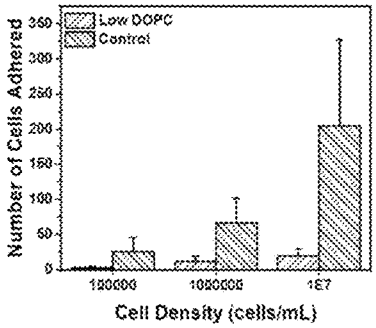
FIG. 8C
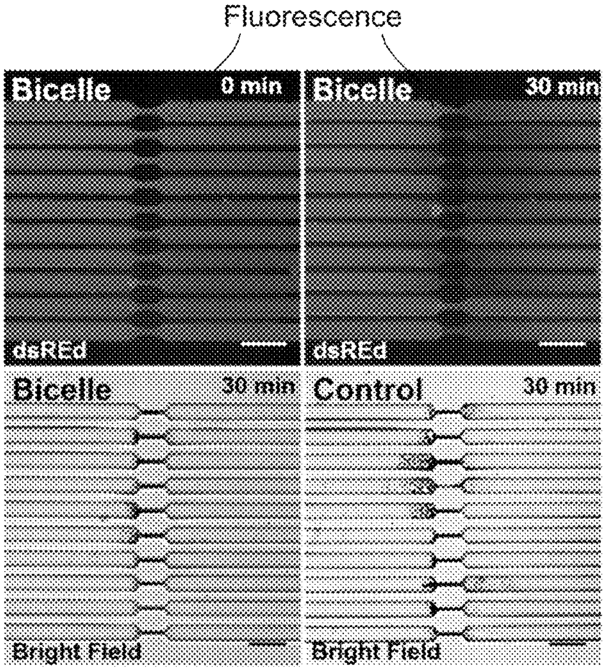
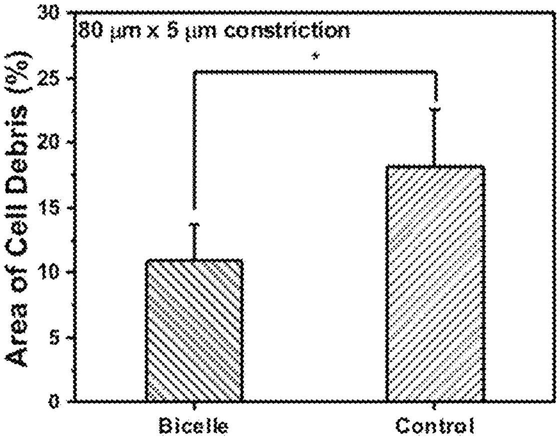
FIG. 9B
FIG. 9A Pre-Start Post 15
Million Cells 6 Hours After
Cell Treatment Post 25 Million Jurkat Cells and Rinse with PBS Bleach and TRIS Rinse Addition of Rhod-Bicelle and TRIS Rinse Post-SDS and TRIS Rinse

HIGH-THROUGHPUT SYSTEM AND METHOD FOR THE TEMPORARY PERMEABILIZATION OF CELLS USING LIPID BILAYERS

RELATED APPLICATION

This Application is a U.S. National Stage filing under 35 U.S.C. § 371 of International Application No. PCT/US2019/047518, filed Aug. 21, 2019, which claims priority to U.S. Provisional Patent Application No. 62/720,734 filed on Aug. 21, 2018, which is hereby incorporated by reference in its entirety. Priority is claimed pursuant to 35 U.S.C. § 119 and any other applicable statute.

TECHNICAL FIELD

The technical field generally relates to devices and methods that are used to deliver molecules or other cargo into cells at clinically relevant scales. The technical field has particular suitability for the delivery of gene-editing constructs or biomolecules into large numbers of cells. In particular, the invention relates to microfluidic devices that use fouling-resistant microchannels that have constrictions therein to temporarily permeabilize cells that aid in the introduction and transfer of molecules or other cargo from the surrounding fluid into the cells.

BACKGROUND

Gene-therapy and gene modification technologies are increasingly being studied, investigated, and applied in fundamental research and for clinical translational applications. In order to modify or to alter genes, the gene-editing biomolecules or other constructs ideally need to be delivered into cells safely, rapidly, and efficiently. Currently, a standard technique for genome modification uses virus-based delivery systems that utilize, for example, lentiviruses, adenoviruses, adeno-associated viruses, or herpes virus. Lentiviruses, for instance, can deliver genetic information into DNA of the host cell so they are one of the most effective and commonly used methods of a gene delivery vector. The use of viral transfection, while effective as a vector system, is expensive, is limited by the size of the desired biomolecular cargo, and has potential serious adverse side effects. Principal among the possible dangers with virus-based delivery systems is the fact that integration of genetic modifications occurs semi-randomly, leading to concern for potential genotoxicity and carcinogenesis through off-target effects. In addition, immunogenicity or the possibility for developing immune tolerance to viral vectors used therapeutically also limits potential clinical applications.

Electroporation, in which an electrical field is applied to cells in order to increase the permeability of the cell membrane, is another technique that has been used to transfect cells for gene therapy based on targeted endonucleases. Conventional electroporation, however, suffers from toxicity problems, the need for specialized reagents and equipment, as well as technical limitations in using this method in scaled-up clinical applications. Chemical transfection methods may also be used for gene-editing applications based on targeted endonucleases.

Still other approaches for the intracellular delivery of biomolecules involving nanoparticles or nanostructures (e.g., nanostraws, carbon nanotubes, or needles) have been demonstrated but have not been commercialized or scaled up for clinical use. Intracellular delivery of biomolecules by cell membrane deformation within microfluidic channels has been demonstrated. For example, U.S. Patent Application Publication No. 2014/0287509 discloses a microfluidic system for causing temporary pertubations in the cell membrane using a cell-deforming constriction in the microfluidic channel. In another approach, a series of microconstrictions are generated by a pattern of protuberances that extend from a polydimethylsiloxane (PDMS) to apply shear and compressive forces on cells passing therethrough. See Han et al., CRISPR-Cas9 delivery to hard-to-transfect cells via membrane deformation., Sci. Adv., pp. 1-8 (2015).

While the intracellular delivery through cell membrane deformation is beginning to emerge, current embodiments of this technology suffer from issues with fouling or clogging, which affects the long-term reliability of the device and efforts for translation towards clinically relevant applications. For example, in clinical gene therapy, large numbers of cells need to be transfected (e.g., billions of cells) rapidly. Current technologies are generally not adapted for such large scale processing because they tend to become quickly fouled or clogged. For example, it is not uncommon for a microfluidic device to become clogged with cells after just seconds or minutes of operation. Attempts have been made to overcome the fouling and clogging issues that arise in the processing of large numbers of cells. For example, International Patent Application Publication No. WO 2018/039084 discloses a method of using microchannels having slippery liquid-infused porous surfaces (SLIPS). In SLIPS, a porous or textured solid contains an immobilized lubricant film that exhibits omniphobic properties. Additional methods and techniques are needed, however, to address the fouling/clogging problem.

SUMMARY

In one embodiment, a microfluidic-based system for the intracellular transport of molecules or other cargo is disclosed. The system includes a microfluidic substrate or chip that includes therein one or more microfluidic channels (e.g., microchannels) that contain one or more constrictions that are dimensioned to induce a transient increase in the permeability of cells that pass through the constrictions. The microchannels may be arranged in parallel in the substrate or chip (or multiple substrates or chips) (e.g., an array) so that cells may be processed in a parallel fashion in a plurality of microchannels. In this regard, large numbers of cells may be processed so that useful quantities of transfected cells may be used for clinical applications.

The dimensions of the constrictions may vary but are typically between around 30% to around 90% smaller than the diameter or largest dimension of the cell of interest that is flowed through the microchannel. In one particular embodiment of the invention, the constriction has a width within the range between about 4 μm to about 10 μm. In order to prevent fouling and/or clogging of the microchannels at the constriction, in one embodiment, the inner walls or surfaces of the microchannels (and constrictions) are coated or otherwise lined with lipid bilayers. In another embodiment, the inner walls or surfaces of the microchannels are coated or lined with hybrid monolayers formed on supporting molecules that resist fouling of the channels and the constriction regions.

In one embodiment, lipid bicelles formed using a long-chain phospholipid component and a short-chain phospholipid component are used to form the lipid bilayers that coat the surfaces of the microchannels. The lipid bicelles are formed and introduced into the microchannels where the bicelles naturally interact with the hydrophilic inner surface (s) of the microchannels and rupture; liberating the short-chain phospholipid component to form the lipid bilayer that conformally coats the one or more surfaces of the microchannels. The formation of the lipid bilayer on the surface(s) of the microchannel is thermodynamically favored and occurs naturally once the lipid bicelles have been loaded into the device.

One method of forming the lipid bicelles uses the freeze-thaw-vortex process disclosed by Cho and co-workers and disclosed in Kolandouzan, K. et al., Optimizing the Formation of Supported Lipid Bilayers from Bicellar Mixtures, *Langmuir* 33, 5052-5064 (2017), which is incorporated by reference herein. In one particular embodiment, the bicelles are formed using the long-chain phospholipid 1,2-dioleoyl-sn-glycero-3-phosphocholine (DOPC) and the short chain 1,2-dihexanoyl-sn-glycero-3-phosphocholine (DHCP). In one particular embodiment, the q-ratio or the molar ratio of the long-chain phospholipid to the short-chain phospholipid (i.e., [DOPC]/[DHCP]) is at about 0.25. The lipid bicelles may be formed using a freeze-thaw-vortex cycle in which the hydrated DOPC/DHCP is plunged into liquid nitrogen for about one (1) minute followed by a five (5) minute incubation period in a warm water bath (e.g., 60° C.) and vortexing for about 30 seconds. This freeze-thaw-vortex may be repeated for several cycles (e.g., five) until the final bicellar mixture is optically clear.

After the one or more microchannels have been coated with the lipid bilayer, cells may then be run through the microfluidic substrate or chip that includes therein one or more microchannels. In one preferred embodiment, large numbers of cells are processed through the device. For example, by using multiple parallel channels (or multiple chips or substrates), in one particular embodiment, all the cells necessary for a 12 kg child's gene-modified bone marrow transplant in 1 hour (estimated at ≥1 billion cells) may pass through the device. This estimate assumes 50,000 cells per sec per microfluidic channel, which has already been reached and can be scaled up to even greater processing speeds by increasing the number of channels per device. This time compares favorably to current electroporation methods that require many hours and significant additional processing steps. Even higher throughputs may be obtainable.

In one embodiment, a microfluidic device for processing cells includes one or more microchannels disposed in a substrate or chip and fluidically coupled to an inlet configured to receive a solution containing the cells along with molecules or other cargo to be delivered intracellularly to the cells, each of the one or more microchannels containing a constriction region therein, wherein the one or more microchannels the respective constriction regions have a lipid bilayer formed on internal surfaces thereof.

In another embodiment, a method of delivering gene-editing molecules to cells includes flowing a solution containing the cells and the gene-editing molecules through one or more microchannels formed in a microfluidic device or chip, wherein each of the one or more microchannels comprises one or more constriction regions, wherein the one or more microchannels and the one or more constriction regions comprise an internal surface or surfaces having a lipid bilayer disposed thereon.

In another embodiment, a method of forming a lipid bilayer on the surfaces of one or more microchannels includes the operations of: providing a microfluidic device having one or more microchannels, the one or more microchannels comprising one or more hydrophilic surfaces; and flowing lipid bicelles into the one or more microchannels formed using a long-chain phospholipid component and a short-chain phospholipid component, wherein the lipid bicelles naturally interact with the one or more hydrophilic surfaces of the one or more microchannels and rupture liberating the short-chain phospholipid component to form a lipid bilayer comprising the long-chain phospholipid component that conformally coats the one or more hydrophilic surfaces. In other embodiments, the lipid bilayer is formed by incubating the bilayer compositions in a polymerization medium and polymerized with ultraviolet (UV) light.

BRIEF DESCRIPTION OF THE DRAWINGS

FIG. 2 illustrates a two-layer device although it should be appreciated that additional layers may be employed in other embodiments (or a single layer).

FIG. 4 illustrates one embodiment of a constriction or constriction region located in a microchannel of the microfluidic substrate or chip. In this embodiment, a lipid bilayer coats the surfaces of the microchannel including the constriction or constriction region.

FIG. 5A schematically illustrates lipid bicelles that are used to form the lipid bilayer on the inner surface of a microchannel. The lipid bicelles rupture and the long-chain phospholipid naturally forms the lipid bilayer on the hydrophilic inner surface of the microchannel.

FIG. 5B illustrates a lipid bilayer being formed on the surface of a solid support (e.g., an inner surface of a microchannel).

FIG. 5C illustrates one method of using the lipid bilayer-coated microchannel for gene-editing applications to target cells that are temporarily permeabilized after passing through lipid bilayer-coated constrictions of a microfluidic device. Cells passing through the lipid bilayer-coated constriction become temporarily permeabilized and molecules or other cargo can enter the cells.

FIG. 8A illustrates fluorescence micrographs of stained Jurkat (Hoescht stained) and genetically modified human embryonic kidney cells (HEKCs) that express fluorescent mitochondria.

FIG. 8B illustrates a graph of the number of Jurkat cells quantified using ImageJ and are shown as a function of flowed cell density. Scale bars: 50 μm.

FIG. 8C illustrates a graph of the number of HEKC cells quantified using ImageJ and are shown as a function of flowed cell density. Scale bars: 50 μm.

FIG. 9A illustrates fluorescence and bright field micrographs of lipid bilayer coated channels before (times 0 minute and 30 minutes) and after treating 500,000 cells with 50 μm×5 μm constricted microfluidic channels.

FIG. 9B illustrates a graph of the area of cell debris for the lipid bilayer coated channels (bicelle) and control (bare channels) which were quantified using ImageJ after treating 25 million cells using 80 μm×5 μm constricted channels. Scale bars: 50 μm.

FIG. 13A illustrates pre-start conditions prior to running cells through the microchannels. Scale bar is 100 μm.

FIG. 15 illustrates how the cells which have been loaded with the intracellular cargo (e.g., molecules or other cargo) are collected/enriched and then introduced into a mammalian subject.

DETAILED DESCRIPTION OF THE ILLUSTRATED EMBODIMENTS

Figure 1:
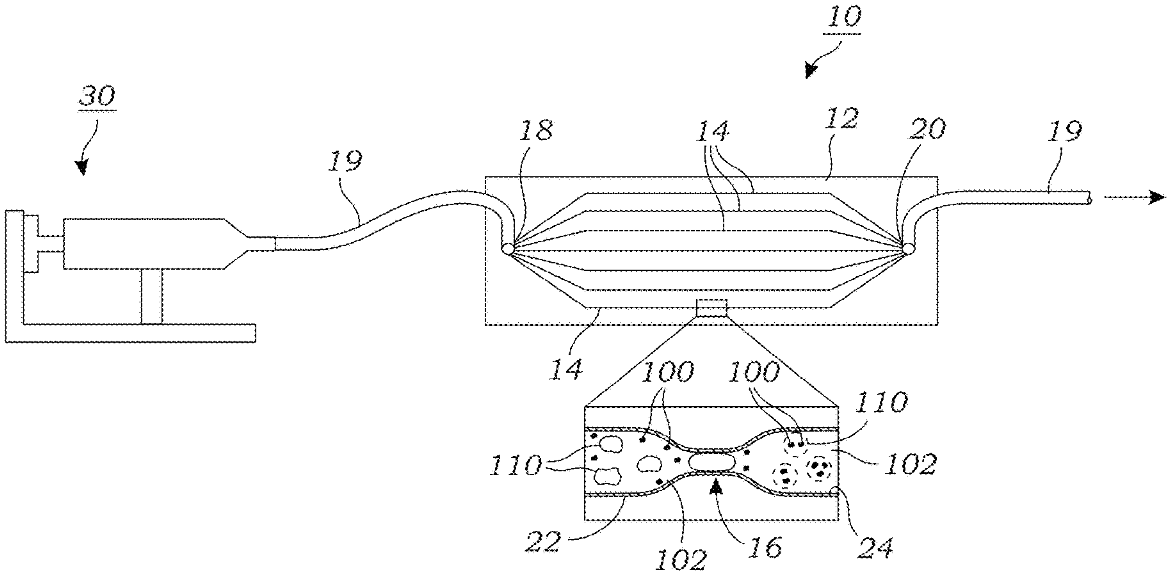
FIG. 1 schematically illustrates a microfluidic-based system for the intracellular transport of molecules or other cargo into cells. Also illustrated (in a magnified view) is a constriction or constriction region that is located in one of the microchannels.

FIG. 1 illustrates a microfluidic-based system 10 for the intracellular transport of molecules or other cargo 100 into cells 110. As explained herein, the cells 110 that receive the molecules or other cargo 100 are living cells 110 that remain live even after passing through the microfluidic-based system 10. The system 10 includes a microfluidic substrate or chip 12 (or multiple substrates or chips 12 in other embodiments) that includes therein one or more microchannels 14 that contain one or more constrictions 16 (or constriction regions) that are dimensioned to induce a transient increase in the permeability of cells 110 that pass through the constrictions 16. In one preferred embodiment, the microfluidic substrate or chip 12 includes a plurality of microchannels 14 that contain one or more constrictions 16. For example, the microfluidic substrate or chip 12 may contain an array of microchannels 14 such as that illustrated in FIGS. 1 and 3 with each microchannel of the array including one or more constrictions 16 formed therein.

The microfluidic substrate or chip 12 may be formed from glass, silicon, or a polymer material and combinations thereof typically used in the construction of microfluidic devices. Exemplary polymer-based materials include, by way of illustration and not limitation, polydimethylsiloxane (PDMS). For example, the microfluidic subsrate or chip 12 may be manufactured using a combination of both glass and PDMS (e.g., PDMS structure containing the microchannels 14 formed therein that is bonded to a glass substrate). The microchannels 14 with the contrictions 16 may be formed in PDMS and then bonded to a glass substrate using well-known PDMS casting techniques. Of course, other methods of manufacture may be used to construct the microfluidic substrate or chip 12. For example, three dimensional printing techniques, laser cutting, mechanical cutting, soft lithography, pipette pulling, or thermal molding may be used to directly form the microfluidic substrate or chip 12 or parts thereof. The microfluidic substrate or chip 12 may be made from multiple layers or a monolithic structure.

Figure 2:
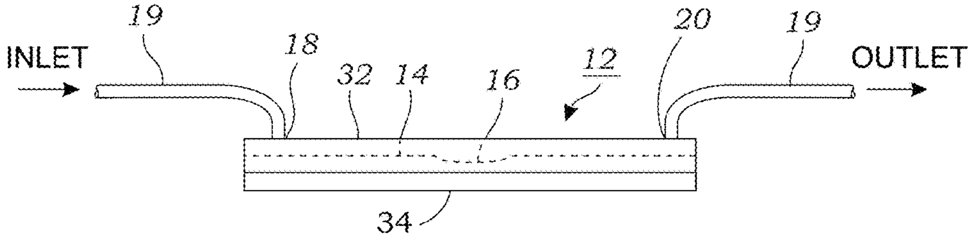
FIG. 2 is a side view of one illustrative construction of the microfluidic substrate or chip that is used as part of the microfluidic-based system.
Figure 3:
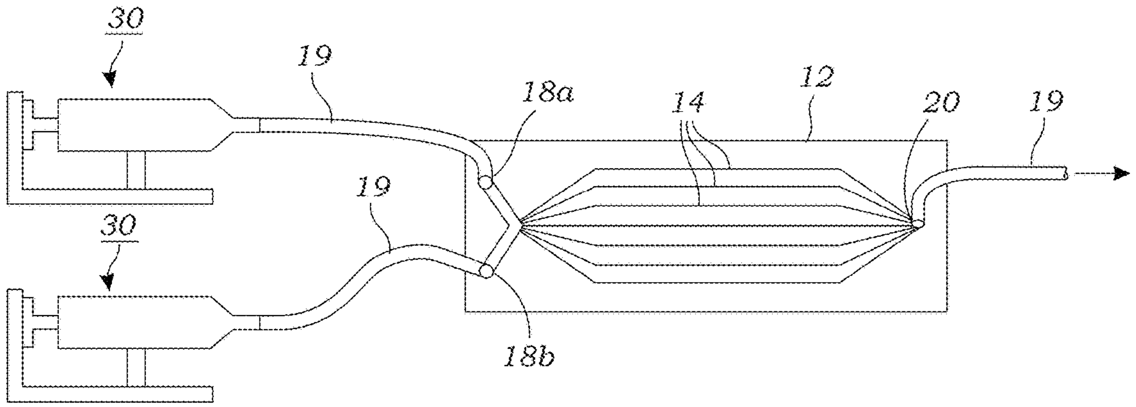
FIG. 3 schematically illustrates a microfluidic-based system for the intracellular transport of molecules or other cargo into cells. In this embodiment, separate pumps are used to pump the cells and the molecules or other cargo that is to be transported into the cells.

As seen in FIGS. 1-3, the microfluidic substrate or chip 12 includes at least one inlet 18 and at least one outlet 20 that are fluidically coupled to the one or more microchannels 14 that are formed within the microfluidic substrate or chip 12. Tubing 19 may be connected to the at least one inlet 18 and the at least one outlet 20 as illustrated. The microchannels 14 form a fluidic path through the microfluidic substrate or chip 12. Generally, the microchannels 14 are rectangular or square in cross-sectional shape and have cross-sectional dimensions that are less than about 1 mm, although it should be understood that other geometric shapes may be used in the microfluidic system 10 described herein. Typically, the cross-sectional dimension of the microchannels 14 at their largest dimension is less than about 250 μm. More typically, the microchannels 14 have a diameter or width that is less than about 50 μm in some embodiments (e.g., around 25

μm×25 μm). The microchannels 14 are dimensioned so as to accommodate the passage of cells 110 contained within a carrying fluid 102. The cells 110 are typically eukaryotic cells and more specifically eukaryotic cells obtained from a mammal (e.g., human). The cells 110 may have a range of sizes but typically have a diameter or largest dimension within the range of around 5 μm to around 20 μm. The length of the microchannels 14 may also vary. The length of the microchannels 14 may be tens or hundreds of microns in length or up to several or tens of centimeters in length.

The microchannels 14 may be linear in shape as illustrated in FIGS. 1 and 3 or they have other configurations such as being curved, spiraled, serpentine, or the like. As seen in FIG. 1, a plurality of microchannels 14 are provided in a single microfluidic substrate or chip 12 to enable parallel processing of cells 110. As seen in FIG. 1, each microchannel 14 contains one or more constrictions 16 located along a length of the microchannel 14. For example, each microchannel 14 may contain a single constriction 16 located along its length. In other embodiments, each microchannel 14 may contain a plurality of such constrictions 16 along a length thereof. The width (W) of the constriction 16 (best seen in FIG. 4) is formed so as to subject the cells 110 to a transient compression or stretching of the cell 110 that temporarily increases the permeability of the cellular membrane of the cells 110 such that the cells 110 uptake the extracellular molecules or cargo 100 that are contained in the surrounding carrying fluid 102.

The uptake of the extracellular molecules or cargo 100 is vector-free and is diffusion based. The width (W) of the constriction(s) 16 may vary but is/are generally less than about 10 μm. For example, the width of a particular constriction 16 may include 4 μm, 5 μm, 6 μm, 7 μm, or 9 μm. Of course, for larger cells 110, the width (W) of the constriction 16 may be larger than 10 μm. The key aspect is that the constriction imparts upon the passing cells 110 a rapid and temporary stretching or compression that temporarily increases the permeability of the cellular membrane of the cells 110. Typically, the constriction 16 may have a width (W) that is about 30% to about 90% smaller than the diameter of the living cell 110 of interest. The length (L) (FIG. 4) of the constriction 16 may vary but is typically within the range of about 10 μm to about 100 μm (e.g., 80 μm). The depth (D) or height of the constriction 16 may be similar the depth (D) or height of the microchannels 14. For example, the depth (D) of the constriction may be around 50 μm or less.

Generally, the increased permeability of the cellular membrane of the living cell 110 lasts hundreds of seconds to several minutes (e.g., about 4-10 minutes is common). As the molecules or other cargo 100 travel with the cells 110 through the microchannels 14 in the surrounding carrying fluid 102, the molecules or other cargo 100 are incorporated intracellularly via diffusion across pores formed in the cell membrane established as the cells 110 pass through the constrictions 16.

As seen in FIG. 1, the molecules or other cargo 100 are initially present within a carrier fluid 102 and are located outside or extracellular with respect to the cells 110. The molecules or other cargo 100 may be added to a culture medium or buffer solution that surrounds the cells 110 and this mixture may be delivered via a common inlet 18 such as that illustrated in FIG. 1. Alternatively, as seen in the embodiment of FIG. 3, the microfluidic substrate or chip 12 may have a first inlet 18*a* that is that is used to deliver cells 110 and a second inlet 18*b* that is used to deliver the molecules or other cargo 100 that are then mixed together in the microfluidic substrate or chip 12. As seen in FIGS. 1 and 3, the microfluidic substrate or chip 12 is coupled to one or more pumps 30 that are used to pump the cells 110 and the molecules or other cargo 100 through the microchannels 14. Any number of types of pumps 30 known to those skilled in the art may be used including, for example, syringe pumps, peristaltic pumps, and the like. The pumps 30 may be controlled or adjustable to modify the flow rate of fluid through the microchannels 14. Generally, the flow rate of fluid 102 through the microchannels 14 is less than 1 mL/minute per microchannel 14. Higher flow rates will produce higher throughputs through the system 10. According to one preferred embodiment of the invention, flow rates that achieve cell processing rates between about 50 and about 100,000 cells/sec/microchannel 14 are used.

The molecules or other cargo 100 may include any number of biomolecules that are desired to be transported into the cells 110. These include, by way of example, proteins, enzymes, nucleic acids (e.g., DNA, RNA), plasmids, and/or combinations of these molecules packaged into nanoparticle-based carriers. Examples of nanoparticle-based carriers include, by way of example, organic platforms such as lipid structures (e.g., liposomes, lipoplexes), polymeric nanoparticles (e.g., cationic polymers, dendrimer-based architectures), carbon nanostructures, and inorganic platforms (e.g., plasmonic, mesoporous metal oxide nanoparticles derived from sol gel chemistry). Molecules or other cargo 100 may also optionally include one or more labels or dyes (e.g., fluorescent label) that may be used to target individual cell types, cell phenotypes, cell genotypes, intracellular organelles located within cells, or cell products. In one particular embodiment, the molecules or other cargo 100 include gene-editing molecules that alter the genetic makeup of the cells 110. One particular example of gene-editing molecules includes the CRISPR-Cas9 nuclease system that includes homologous template DNA (donor template DNA), single-guide RNA (sgRNA) (ribonucleoprotein-guide RNA complexes) and the enzyme Cas9. The sgRNA directs the Cas9 nuclease to introduce sequence-specific targeted insertions, deletions, and genetic edits at specific genetic targets of the cells 110.

FIG. 2 illustrates the construction of the microfluidic substrate or chip 12 according to one embodiment. In this embodiment, the microfluidic substrate or chip 12 is formed from a laminate structure having multiple layers that adhered or otherwise bonded to one another (e.g., polymer layers that are bonded together). As seen in FIG. 2, a first layer 32 of the device has the microchannels 14 with constrictions 16 formed therein that is bonded or adhered to a second layer 34 that serves as the bottom (or top) of the device. The at least one inlet 18 and at least one outlet 20 are also formed in the first layer 32. Tubing 19 may be connected to the inlet 18 and outlet 20 as illustrated. In one embodiment of the microfluidic substrate or chip 12, both the first layer 32 and the second layer 34 are formed from the same material. In another embodiment, the first layer 32 may be formed from a first material while the second layer 34 is formed from a second, different material (e.g., glass and PDMS).

The one or more the surfaces 22 of the microchannel 14 (and constriction 16) that are exposed to the carrying fluid 102 containing the cells 110 and molecules or other cargo 100 include a lipid bilayer 24 that is disposed on the one or more surfaces 22 (or multiple lipid bilayers 24). The presence of the lipid bilayer 24 on the one or more surfaces 22 imparts anti-fouling properties to the microfluidic substrate or chip 12 and allows large numbers of cells 110 to be processed without premature clogging of the microchannels 14 and/or constrictions 16. The presence of the lipid bilayer 24 extends the life of the microfluidic substrate or chip 12 prior to requiring disposal or cleaning (e.g., as described herein and illustrated in FIGS. 14A-14D). The one or more surfaces 22 may include all or a portion of the surfaces 22 that form the microchannel 14 and/or constrictions 16. For example, in a microchannel 14 with a rectangular cross-section that contains four (4) surfaces 22 (e.g., bottom, top, and two sides) and each surface 22 may support a lipid bilayer 24. This is illustrated in FIGS. 1, 4 and 5C. FIG. 4 illustrates a cross-sectional view of a microchannel 14 and constriction 16 that contains the lipid bilayer 24 disposed along the inner surface 22. FIG. 5C illustrates one embodiment in which stem cells 110 are run through the microfluidic substrate or chip 12 and undergo temporary permeabilization after passing through the lipid bilayer-coated constrictions 16. Gene-editing cargo 100 or vectors are then able to enter the interior of the target cells as seen in FIG. 5C.

To make the lipid bilayer 24, lipid bicelles 26 (seen in FIG. 5C) are formed using a long-chain phospholipid component (e.g., DOPC) and a short-chain phospholipid component (e.g., DHCP) are used to form the lipid bilayers 24 that coat the surface(s) 22 of the microchannels 14. Lipid bicelles 26 are disk-shaped aggregates formed from long-chain phospholipids that make up a flat or planar region of the structure and either detergent or short-chain phospholipids that form the edges or rim of the structure. The lipid bicelles 26 are formed and introduced into the microchannels 14 where the bicelles 26 naturally interact with the hydrophilic surface(s) 22 of the microchannels 14 and rupture; liberating the short-chain phospholipid component (FIG. 5B) to form the lipid bilayer 24 that conformally coats the one or more surfaces 22 of the microchannels 14 as seen in FIGS. 4, 5B, and 5C. As seen in FIGS. 5B and 5C, the long-chain phospholipid component (e.g., DOPC) forms the lipid bilayer 24 on the one or more surfaces while the short-chain phospholipid component (e.g., DHCP) is liberated and exits the microchannels 14. The surface(s) 22 of the microchannels 14 may be naturally hydrophilic or rendered hydrophilic, for example, by exposure to oxygen plasma, Piranha solution, or the like. The surface charge of the bicelles 26 (and the resulting lipid bilayer 24 that is formed) may be tuned by the choice of long-chain phospholipid component. For example, long-chain lipids with negatively charged headgroups may be used as one example.

Figure 6:
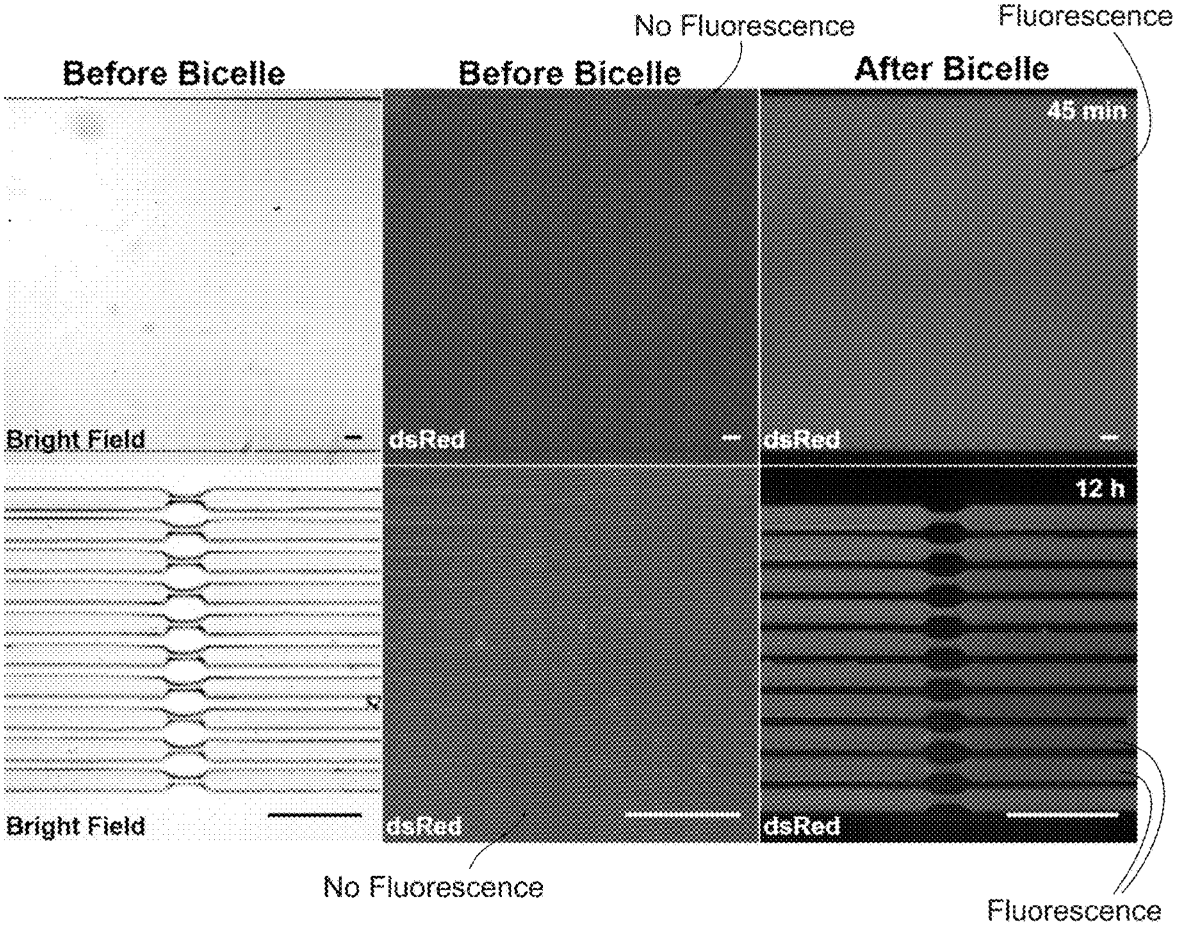
FIG. 6 illustrates bright field (left column) and fluorescence micrographs of microfluidic channels before and after being coated with fluorescently-labeled lipid bilayers using bicellular mixtures. Scale bars: 100 μm.

The formation of the lipid bilayer 24 on the surface(s) 22 of the microchannel(s) 14 is thermodynamically favored and occurs naturally once the lipid bicelles 26 have been loaded into the substrate or chip 12. FIG. 6 illustrates fluorescence micrographs (before and after exposure to lipid bicelles 26) of microchannels 14 coated with fluorescently labeled lipid bilayers 24 using bicellular mixtures. Before exposure to the bicelles 26, the microchannels 14 do not fluoresce in the red channel (middle column). After exposure to the bicelles 26, the microchannels 14 fluoresce in the red channel (right column) due to the formation of the lipid bilayer 24 on the surfaces 22 of the microchannel 14.

An exemplary process of making the bicelles 26 and forming the lipid bilayer 24 is described below. In one embodiment, 1,2-dioleoyl-sn-glycero-3-phosphocholine (DOPC) and 1,2-dihexanoyl-sn-glycero-3-phosphocholine (DHPC) purchased from Avanti Polar Lipids (Alabaster, AL) are used to make the bicelles 26. Small aliquots (200 μL) of DOPC and DHPC dissolved in chloroform are dried separately in test tubes under a gentle stream of nitrogen, while being rotated to make a lipid film at the bottom of the tube. The dried lipid film is then put in a vacuum desiccator (specifically for lipid use) overnight. Next, the DOPC film is hydrated (10 mM TRIS, 150 mM NaCl, pH 7.5) to a concentration of 63 μM to make a DOPC stock solution (20.192 mL of TRIS in 1 mg). The DOPC solution is then used to hydrate the DHPC film to where the final concentration of DHPC is 0.252 mM (8.75 mL of DOPC stock per 1 mg), such that the molar ratio ("q-ratio") DOPC:DHPC is 0.25 between long and short chained lipids. Generally, any concentration that keeps DHPC below its critical micelle concentration (CMC) will work. A q-ratio of 2.5 also generates good lipid bilayers 24. The lipid mixture is next transferred to 50 mL falcon tubes and a small hole is punctured in the top using an 18-gauge syringe needle to alleviate pressure. The sample is then plunged into liquid nitrogen for 1 min, followed by a 5-min incubation in a 60° C. water bath (prepared on a hotplate prior to hydration) and vortexing for 30 s. This freeze-thaw-vortex cycle is repeated five times, yielding a product that is optically transparent. Lipid bilayers 24 on the surfaces 22 of the microchannels 14 are formed by flowing the bicelle 26 solution into the microchannel(s) 14 using a syringe pump with a flow rate of 20 uL/min for 45 min (See FIGS. 5A and 5B). This is followed by a washing step with a constant flow of TRIS buffer (50 uL/min), for another 30 min.

In an alternative embodiment, bicelles 26 are prepared with the same concentrations as the method above but instead of using DOPC as the long-chain phospholipid 1,2-bis[10-(2',4'-hexadienoyloxy)decanoyl]-sn-glycero-3-phosphocholine (bis-SorbPC) is used. The bicelles 26 are then flowed into the microchannels 14 using the aforementioned flow rates and washed with TRIS buffer. These new bilayer compositions are then incubated in the polymerization medium (100 mM $K_2S_2O_8$/10 mM $NaHSO_3$, saturated with Argon (or Nitrogen)) with ultraviolet (UV) irradiation for 2 hours without exposing the bilayer to air and then washed with TRIS buffer (50 uL/min). In this alternative embodiment, the lipid bilayer 24 is polymerized by application of UV light. In addition, this change in lipid molecule can improve the viscoelastic properties of the system and maintain the non-fouling zwitterionic nature of the bilayer.

The microchannels 14 as well as the constriction 16 may be formed using any number of methods known to those skilled in the art for forming features in microfluidic devices. This includes three-dimensional printing, laser cutting, mechanical cutting, soft lithography, pipette pulling, or thermal molding. In one particular method of making the microchannels 14, a direct casting method is employed wherein the microchannels 14 as well as the constriction 16 are formed in PDMS which is then bonded to a glass substrate after exposure to surface oxygen plasma. The exposure to oxygen plasma also aids if ensuring the hydrophilic nature of the inner surface(s) 22 of the microchannels 14 and the constriction 16 which is needed to form the lipid bilayer 24.

Figures 7A, 7B, 7C:
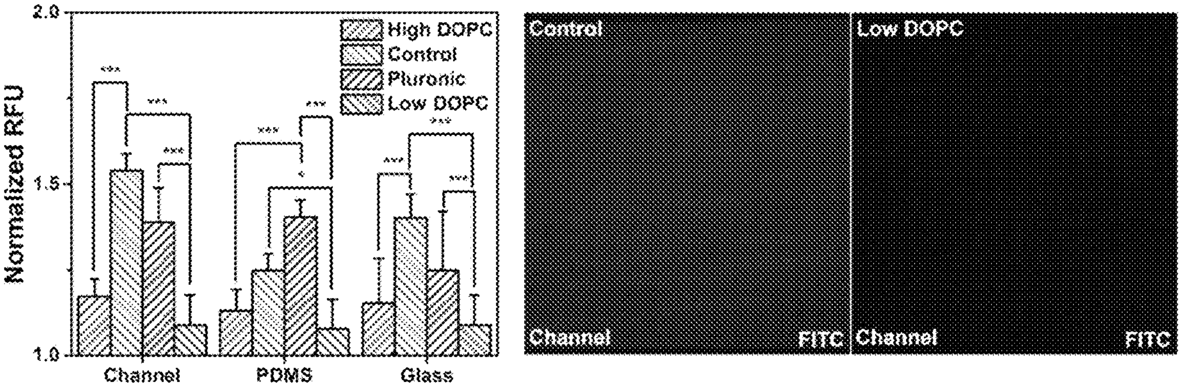
FIG. 7A illustrates measured fluorescence intensity normalized to the background for fluorescence micrographs (normalized relative fluorescence units (RFU)) of the combined and separated characterization device (PDMS and glass) after introducing fluorescein isothiocyanate (FITC)-labeled bovine serum albumin. (Low DOPC 63 μM DOPC; High DOPC_2 mM DOPC). Low DOPC refers to μM levels while High DOPC refers to mM levels.
FIG. 7B illustrates a fluorescence micrograph of a bare microfluidic channel (control) after being exposed to FITC-labeled bovine serum albumin.
FIG. 7C illustrates a fluorescence micrograph of a lipid bilayer-coated microfluidic channels after being exposed to FITC-labeled bovine serum albumin.

The lipid bilayers 24 are biomimietic, biocompatible, demonstrate anti-fouling behavior, and are capable of preventing adhesion of cells 110 on a variety of materials. The bicelle-mediated lipid bilayer 24 reduces the amount of adsorbed protein and prevents adhesion from multiple cell lines (see e.g., FIGS. 7A-7C and 8A-8C). FIGS. 7A-7C, for example, illustrates that lipid bilayer-coated micochannels 14 resists the adhesion of FITC-labeled bovine serum albumin (BSA). In FIG. 7A, for the channel, PDMS, and glass strucures, the lipid bilayer 24 (at both high and low DOPC levels) showed reduced fluorescence. Low DOPC showed the lowest levels of fluorence as compared to high DOPC. FIG. 7C illustrates the lack of fluorescence of the microchannel 14 coated with lipid bilayer 24 (low DOPC). FIGS. 8A-8C illustrate how a lipid bilayer 24 coated onto microchannels 14 results in a significant (>90%) reduction of cell adhesion. FIG. 8A illustrates fluorescence micrographs of stained Jurkat (Hoescht stained) and genetically modified human embryonic kidney cells (HEKCs) for both the surfaces 22 containing the lipid bilayer 24 and a control surface (with no lipid bilayer 24). FIG. 8B illustrates a graph of the number of Jurkat cells quantified using ImageJ imaging software and are shown as a function of flowed cell density. Scale bars: 50 μm. FIG. 8C illustrates a graph of the number of HEKC cells quantified using ImageJ imaging software and are shown as a function of flowed cell density. Scale bars: 50 μm. A significant reduction in number of adhered cells 110 is seen for both cell types.

Moreover, there is considerably less cell debris at the microfluidic constrictions 16 coated with the lipid bilayer 24 after processing large numbers of cells 110 (e.g., 25 million cells). FIG. 9A illustrates bright field and fluorescence micrographs of lipid bilayer 24 coated microchannels 14 before (upper left) and after (upper right) treating 500,000 cells with 50 μm×5 μm constricted microchannels 14. Further, the area of cell debris was quantified as seen in FIG. 9B using ImageJ image processing software for both bare (control) and lipid bilayer 24 coated microchannels 14 after treating 25 million cells using 80 μm×5 μm constricted channels. The area of cell debris was significantly lower for the microchannels 14 containing the lipid bilayer 24.

Figure 10:
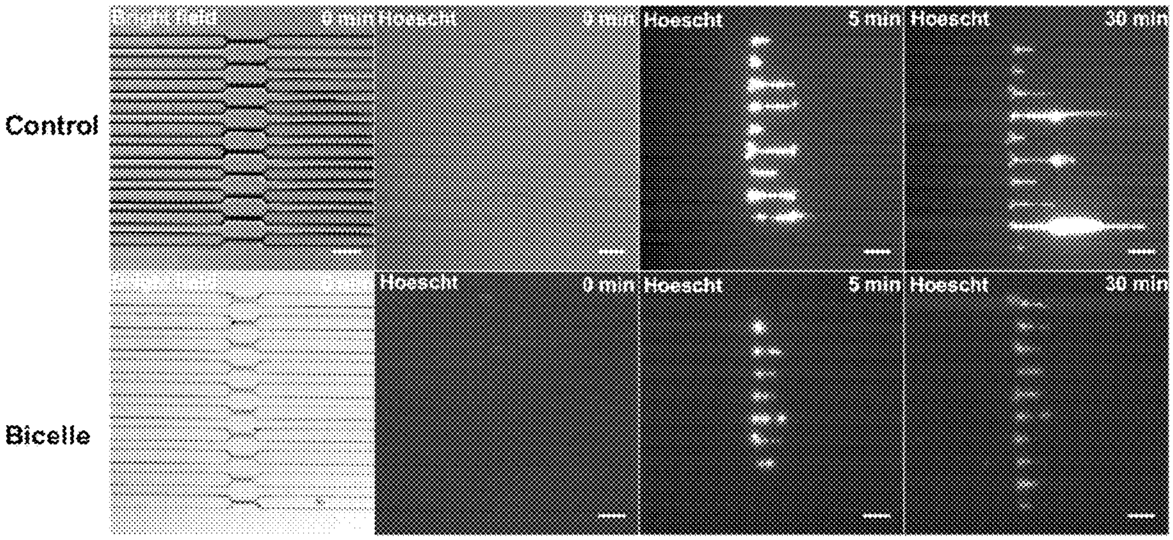
FIG. 10 illustrates bright field and fluorescence micrographs of bare (control) and lipid bilayer-coated channels (bicelle) before and after treating 500,000 Jurkat cells with a nuclear stain (Hoescht) using constricted microfluidic channels. Bright areas (right two columns) represent residual nuclear debris from cells that have ruptured after passing through channel constrictions. Scale bars: 50 μm.

FIG. 10 illustrates bright field and fluorescence micrographs of bare (control) and lipid bilayer 24 coated microchannels 14 (bicelle) before and after treating 500,000 Jurkat cells with a nuclear stain (Hoescht) using microfluidic channels 14 with constrictions 16. Bright areas represent residual nuclear debris from cells 110 that have ruptured after passing through channel constrictions 16. The non-bicelle control (top) clearly illustrates a higher level of cell debris (e.g., brighter areas in image) as compared to microfluidic channels 14 coated with the lipid bilayer 24.

The physicochemical properties of these bilayers can also be controlled by tailoring the composition of the lipid components to have specific electrostatic or chemical interactions with macromolecules and cells 110. For example, surface charges may tuned or changed in the surface membrane to aid the anti-fouling capability of the lipid bilayer 24 coating on the surface 22 of the microchannel 14. For example, the lipid bilayer 24 may be rendered neutral, negative, or positive by varying the lipid composition of the lipid bilayer 24. Lipids having different charge characteristics may be added incorporated into the bicelles. For example, some lipids such as 1,2-dioleoyl-sn-glycero-3-ethylphosphocholine (chloride salt) (DOEPC) and 1,2-dioleoyl-3-trimethylammonium-propane (chloride salt) (DOTAP) are positively charged lipids. 1-palmitoyl-2-oleoyl-sn-glycero-3-phospho-(1'-rac-glycerol) (sodium salt) (POPG) is a negatively charged lipid. 1,2-dioleoyl-sn-glycero-3-phosphocholine (DOPC) is a zwitterionic lipid. The different molar ratios of the various constituent phospholipids may be adjusted to tune the resulting charge of the lipid bilayer 24. Additional examples of phospholipids and detergents usable to create bicelles 26 include, for example, 1,2-Dimyristoyl-sn-Glycero-3-Phosphocholine (DMPC)/[3-[(3-Cholamidopropyl)-Dimethylammonio]-1-Propane Sulfonate]•N,N-Dimethyl-3-Sulfo-N-[3-[[3a,5b,7a,12a)-3,7,12-Trihydroxy-24-Oxocholan-24-yl] Amino]propyl]-1-Propanaminium Hydroxide, Inner Salt] (CHAPS) and 1,2-Dimyristoyl-sn-Glycero-3-[Phosphorac-(1-Glycerol)] (Sodium Salt) (DMPG)/[3-[(3-Cholamidopropyl)dimethylammonio]-2-Hydroxy-1-Propanesulfonate] (CHAPSO), available from Anatrace Products, LLC (Maumee, Ohio).

Figure 11A:
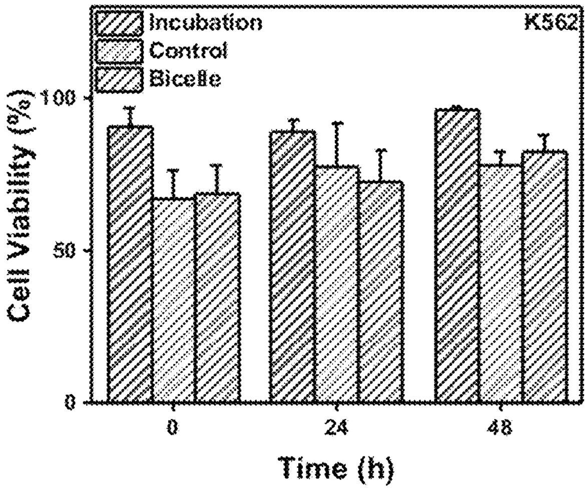
FIG. 11A illustrates cell viability of 40 kDa dextran to K562 cells. Cells were flowed at 300 μL/min at a density of 3 million cells/mL.
Figure 11B:
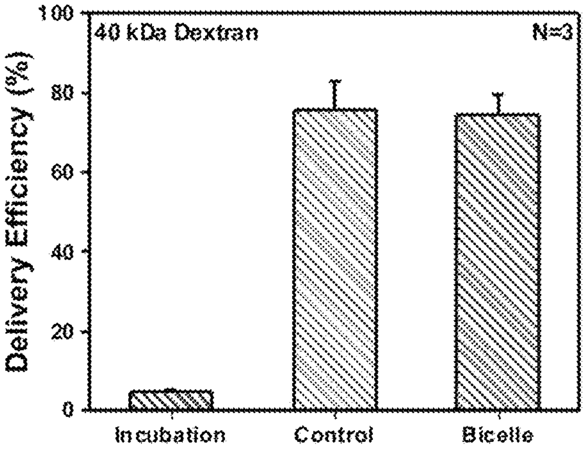
FIG. 11B illustrates delivery efficiency of 40 kDa dextran to K562 cells. Cells were flowed at 300 μL/min at a density of 3 million cells/mL.
Figure 12A:
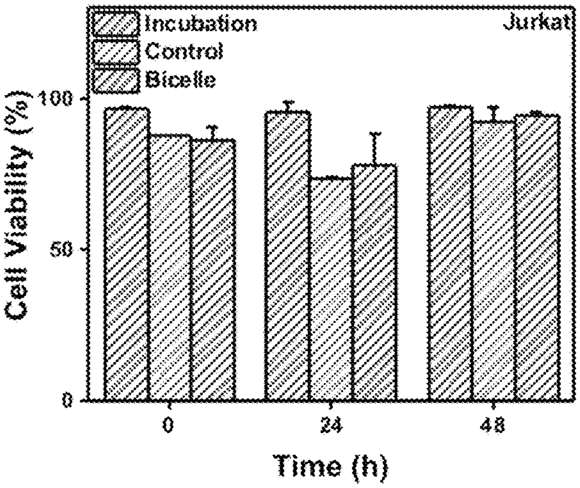
FIG. 12A illustrates cell viability of 40 kDa dextran to K562 cells Jurkat cells. Cells were flowed at 300 μL/min at a density of 3 million cells/mL.
Figure 12B:
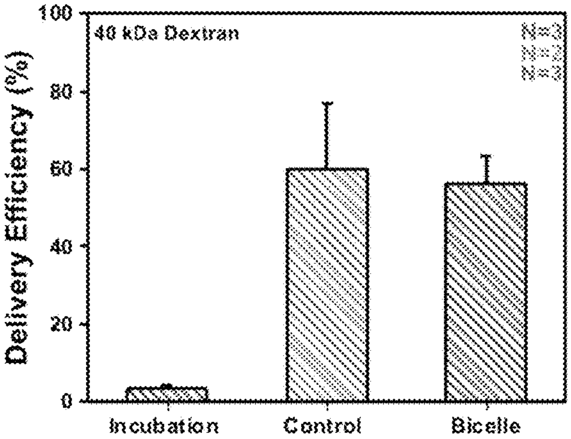
FIG. 12B illustrates delivery efficiency of 40 kDa dextran to K562 cells Jurkat cells. Cells were flowed at 300 μL/min at a density of 3 million cells/mL.

Experiments using microchannels 14 coated with lipid bilayers 24 have validated the intracellular transport capabilities of passivated lipid bilayer 24 microfluidic devices. The microfluidic-based system 10 has successfully been used for the intracellular delivery and successful insertion of 40 kDa fluorescently labeled dextran molecules to Jurkat and K562 cells, which was significantly higher than incubating cells 110 with the dextran (FIGS. 11B and 12B showing delivery efficiencies). For both cell lines, viability increased after 48 hours of incubation and delivery efficiency was found to be greater than 60% for both Jurkat and K562 cells 110 as seen in FIGS. 11A and 12A. These model lymphocyte and leukemia lines were selected based on their reputation for being notoriously difficult to electroporate (a competing technology platform). The intracellular delivery was characterized quantitatively by confocal laser scanning microscopy and flow cytometry.

Figure 13A:
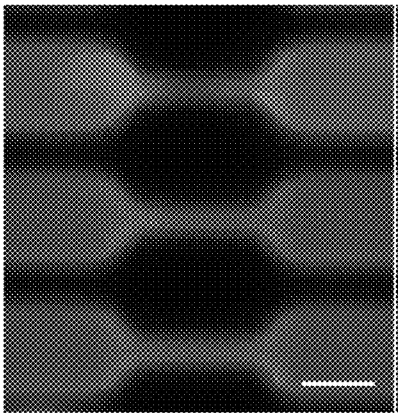
FIG. 13A illustrates a fluorescence micrograph of the constriction regions of several microchannels having a fluorescently stained lipid bilayer.
Figure 13B:
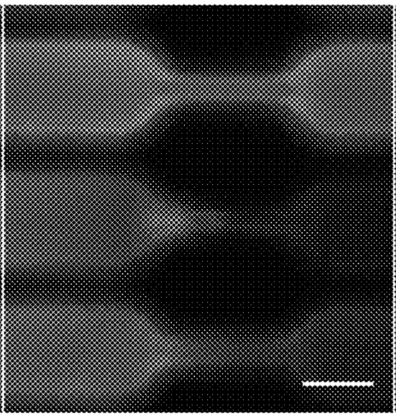
FIG. 13B illustrates a fluorescence micrograph of same region of FIG. 13A after processing 15 million cells. The “dark” regions in the microchannel and constrictions represent areas where the lipid bilayer has delaminated from the microchannel. Scale bar is 50 μm.
Figure 13C:
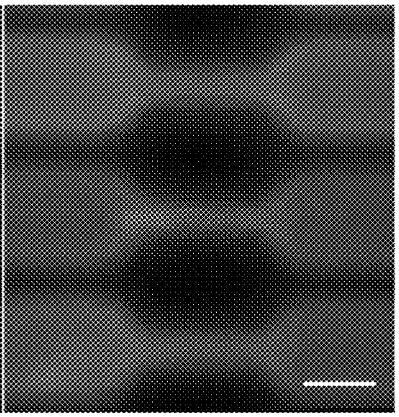
FIG. 13C illustrates the same view of FIGS. 13A and 13B after the device was allowed to sit for six (hours) after flowing cells through the microchannels. Scale bar is 25 μm.

FIGS. 13A-13C illustrate fluorescent micrographs of microchannels 14 their corresponding constrictions 16 coated with a Rhodamine-containing lipid bilayer 24. FIG. 13A illustrates a "pre-start" condition prior to flowing any cells 110 through the microchannels 14. FIG. 13B illustrates the same view of FIG. 13A but after 15 million cells 110 have been processed through the microchannels 14. Darkened areas show regions were the lipid bilayer 24 has delaminated form the surface 22 of the microchannels 14 and constrictions 16. FIG. 13C illustrates the same view of FIG. 13A after the device was allowed to sit for six (hours) after flowing cells 110 through the microchannels 14. As seen in FIG. 13C, the lipid bilayer 24 has returned and "healed" itself. This shows the ability of the lipid bilayer 24 to reform or otherwise heal itself after undergoing partial delamination from the surfaces 22 of the microchannels 14 and constrictions 16.

Figure 14A:
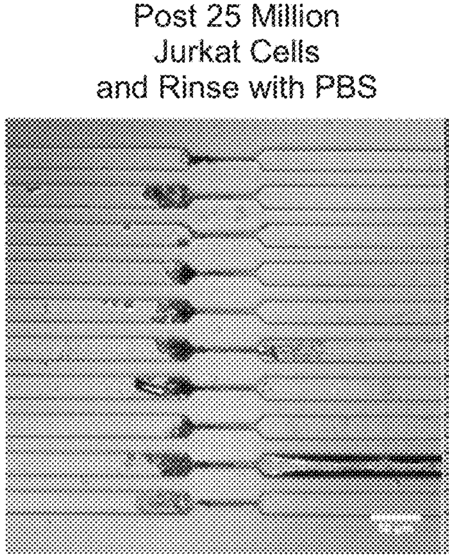
FIG. 14A illustrates a bright field micrograph of several microchannels and their respective constriction regions after processing 25 million Jurkat cells and rinsed with phosphate buffered saline (PBS). Scale bar is 50 μm.
Figure 14B:
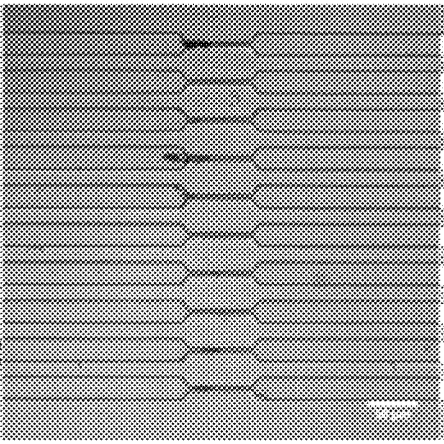
FIG. 14B illustrates a bright field micrograph of the same region of FIG. 14A after flowing bleach and tris(hydroxymethyl)aminomethane (TRIS) rinse through the microchannels. Scale bar is 50 μm.
Figure 14C:
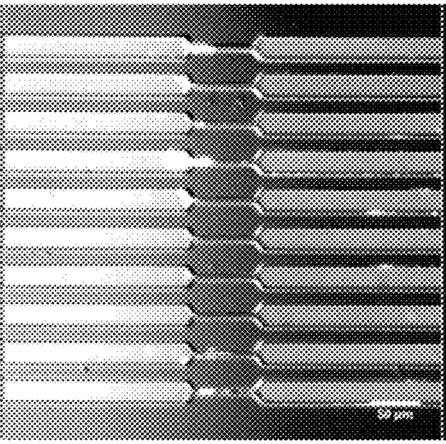
FIG. 14C illustrates a bright field micrograph of the same region of FIG. 14A after flowing Rhodamine-containing bicelles following rinse with TRIS. Scale bar is 50 μm.
Figure 14D:
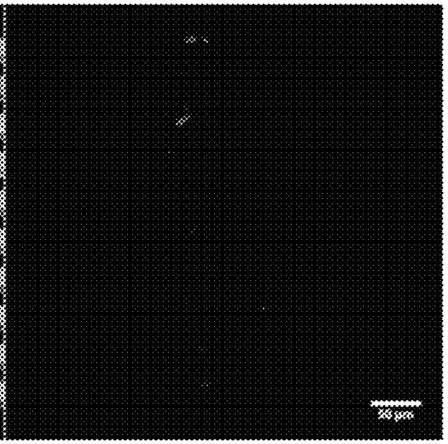
FIG. 14D illustrates a bright field micrograph of the same region of FIG. 14A after sodium dodecyl sulfate (SDS) and TRIS rinse. The lipid bilayer has been stripped or removed from the microchannels. Scale bar is 50 μm.

FIGS. 14A-14D illustrate how the microfluidic-based system 10 can be reused. More specifically, a microfluidic substrate or chip 12 that includes microchannels 14 and constrictions 16 can be cleaned, rinsed, and re-coated with lipid bilayers 24. FIG. 14A illustrates a bright filed image of a microfluidic substrate or chip 12 after 25 million cells have been run through the microchannels 14. Some build-up of cells 110 is seen. FIG. 14B illustrates these same microchannels 14 after bleach and TRIS buffer has been used to rinse the microchannels 14. FIG. 14C illustrates the same microchannels 14 after Rhodamine labeled bicelles 26 were run through the microchannels 14 followed by TRIS buffer rinse. The microchannels 14 clearly show a new lipid bilayer 24 that is deposited onto the surface(s) 22 of the microchannels 14 and constrictions 16. FIG. 14D illustrates the same microchannels 14 after being stripped of the lipid bilayer 24 by sodium dodecyl sulfate (SDS) followed by TRIS rinse.

Thus, even though the presence of the lipid bilayer 24 greatly extends the operational life of the microfluidic substrate or chip 12, there may instances where the microchannels 14 or constrictions 16 still become clogged with cells 110 or cellular debris. In one embodiment, a cleaning solution or series of solutions (e.g., bleach and TRIS buffer as noted above) is run through the microchannels 14 to remove the old lipid bilayer 24 and a new lipid bilayer 24 may be deposited within the microchannels 14 and constriction regions 16. The microfluidic substrate or chip 12 can then be used again. Of course, the microfluidic substrate or chip 12, in another embodiment, may be made a disposable component and discarded after clogging.

Figure 15:
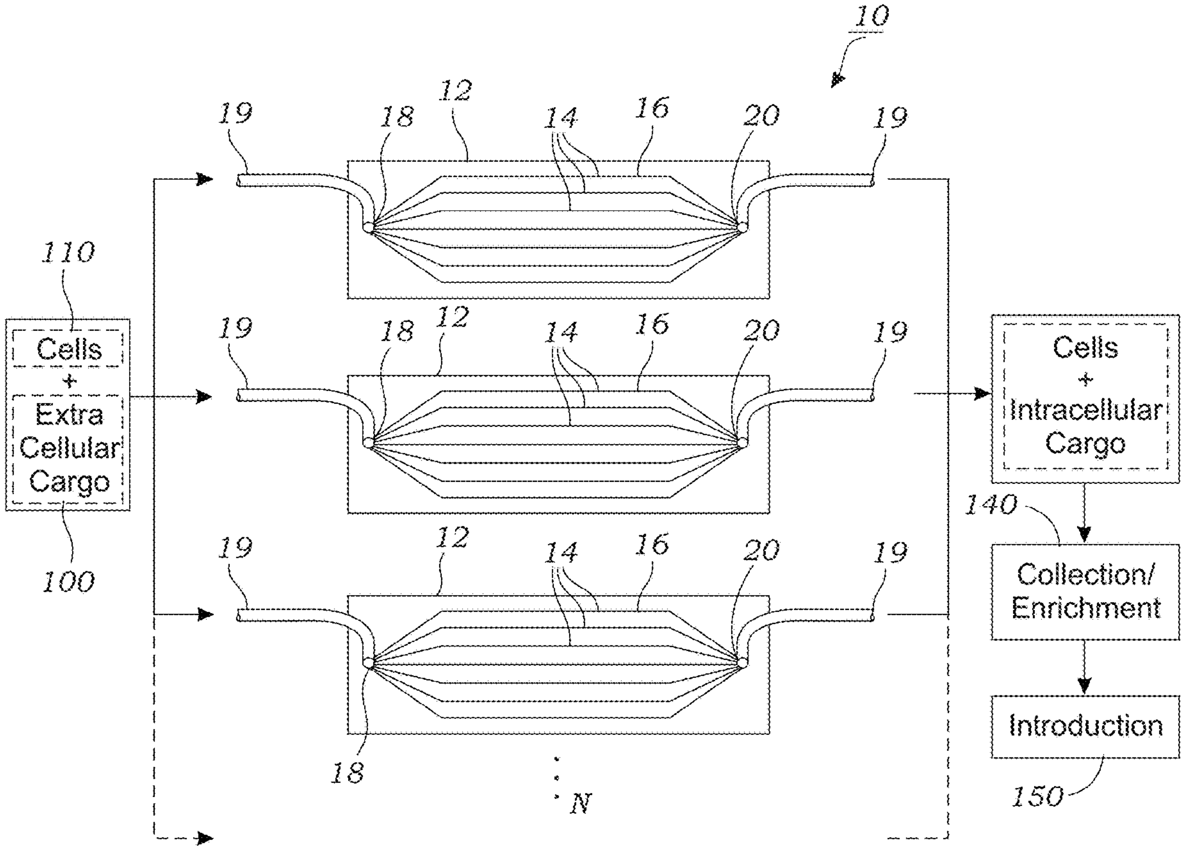
FIG. 15 schematically illustrates a microfluidic-based system for the intracellular transport of molecules or other cargo into cells that uses a plurality of microfluidic substrates or chips in parallel to process large numbers of cells.

FIG. 15 illustrates a schematic representation of a microfluidic-based system 10 for the intracellular transport of molecules or other cargo 100 into cells 110. As seen in FIG. 15, the cells 110 and the molecules or other cargo 100 are run through one or more microfluidic substrates or chips 12. In this particular embodiment, a plurality of microfluidic substrates or chips 12 (N is the total number of microfluidic substrates or chips 12) are employed in parallel so that large numbers of cells 110 may be processed. As explained herein, according to one preferred embodiment of the invention, flow rates that achieve processing rates of cells 110 between about 50 and about 100,000 cells/sec/microchannel may be achieved. Preferably, the microchannel 14 and the constriction region 16 remain unclogged after the passage and sustainable processing (i.e., the cells 110 remain live) of $1\times10^6$ cells, and more preferably more than $1\times10^7$, $1\times10^8$, and $1\times10^9$ cells through the microchannel 14.

The cells 110 may be obtained from a mammalian subject, for example, a human. The cells 110 may include, as one example, stem cells or cells with stem-like properties that are obtained for example, from the bone marrow of a subject. In one preferred embodiment, the cells 110 are living cells and remain living after intracellular delivery of the molecules or other cargo 100. The cells 110 may also include immune cells that are obtained from a subject. An example includes T-lymphocytes that are obtained from the subject for adoptive cellular therapies. The invention is not, however, limited to use with stem cells or immune cells. In other embodiments, other eukaryotic cells types 110 may also be run through the system 10. As noted herein, the cells 110 are run through the microfluidic substrates or chips 12 along with the molecules or other cargo 100 that are to be intracellularly transported into the cells.

The permeabilized cells 110 that uptake the molecules or other cargo 100 are then captured or collected after passing through the microfluidic substrates or chips 12. This is illustrated in operation 140 in FIG. 15. For example, the outlets 20 may be coupled to a collection container (not shown) or other receptacle (e.g., bag, vial(s), bottle(s)) which may be used to enrich the concentration of collected cells 110 that are processed using the system 10. In one embodiment, for example, where the molecules or other cargo 100 include gene-modification components, the collected cells 110 that have been modified genetically may then be introduced into a subject as seen in operation 150. The subject that receives the processed cells 110 may be the same individual that provided the cells 110 that were initially processed with the system 10 (e.g., autologous cells 110). Alternatively, the recipient of the cells 110 may be a different subject from the source of cells 110 that are run through the system 10 (e.g., allogenic cells 110).

While embodiments of the present invention have been shown and described, various modifications may be made without departing from the scope of the present invention. It should be appreciated that multiple lipid bilayers 24 may develop, in some instances, on the surface(s) 22 of the microchannels 14. The use of the term lipid bilayer 24 would encompass such configurations or states because the surface(s) 22 still is coated with at least one lipid bilayer 24. The invention, therefore, should not be limited except to the following claims and their equivalents.

What is claimed is:

1. A microfluidic device for processing cells comprising: one or more microchannels disposed in a substrate or chip and fluidically coupled to an inlet configured to receive a solution containing the cells along with molecules or other cargo to be delivered intracellularly to the cells, each of the one or more microchannels containing a constriction region therein having a width within the range of about 4 μm to about 10 μm, wherein the one or more microchannels and the respective constriction regions have a lipid bilayer formed on internal surfaces thereof.

2. The microfluidic device of claim 1, the substrate or chip further comprising a second inlet fluidically coupled to the one or more microchannels, wherein the second inlet is coupled to a second pump configured to pump a solution containing the molecules or other cargo to be intracellularly delivered into the cells.

3. The microfluidic device of claim 1, wherein the one or more microchannels comprises a plurality of microchannels disposed in the substrate or chip.

4. The microfluidic device of claim 1, wherein the lipid bilayer is positively charged.

5. The microfluidic device of claim 1, wherein the lipid bilayer is negatively charged.

6. The microfluidic device of claim 1, wherein the lipid bilayer is uncharged or substantially uncharged.

7. The microfluidic device of claim 1, wherein the lipid bilayer is zwitterionic.

8. The microfluidic device of claim 1, wherein the lipid bilayer comprises phospholipid 1,2-dioleoyl-sn-glycero-3-phosphocholine (DOPC).

9. The microfluidic device of claim 1, wherein the lipid bilayer comprises 1,2-bis[10-(2',4'-hexadienoyloxy) decanoyl]-sn-glycero-3-phosphocholine (bis-SorbPC).

10. A system for processing cells comprising one or more microfluidic devices of claim 1, further comprising one or more pumps configured to simultaneously pump a solution containing the cells and the molecules or other cargo to be intracellularly transported into the cells through the one or more microfluidic devices.

11. A method of using the microfluidic device of claim 1, comprising:

flowing in the one or more microchannels a solution containing the cells and the molecules or other cargo to be intracellularly delivered into the cells.

12. The method of claim 11, wherein the molecules or other cargo comprise gene-editing biomolecules.

13. The method of claim 11, wherein the gene-editing biomolecules comprise clustered regularly interspaced short palindromic repeats (CRISPR)-Cas9 biomolecules including ribonucleoprotein-guide RNA complexes and donor template DNA.

14. The method of claim 11, wherein the one or more microchannels remain unclogged after passage of $1\times10^6$ cells through the plurality of microchannels.

15. A method of delivering gene-editing molecules to cells comprising:

flowing a solution containing the cells and the gene-editing molecules through one or more microchannels formed in a microfluidic device or chip, wherein each of the one or more microchannels comprises one or more constriction regions having a width within the range of about 4 μm to about 10 μm, and wherein the one or more microchannels and the one or more constriction regions comprise an internal surface or surfaces having a lipid bilayer disposed thereon.

16. The method of claim 15, wherein the gene-editing molecules are packaged into nanoparticle carriers.

17. The method of claim 15, wherein the lipid bilayer is positively charged.

18. The method of claim 15, wherein the lipid bilayer is negatively charged.

19. The method of claim 15, wherein the lipid bilayer is uncharged or substantially uncharged.

20. The method of claim 15, wherein the lipid bilayer is zwitterionic.

21. The method of claim 15, wherein the lipid bilayer comprises phospholipid 1,2-dioleoyl-sn-glycero-3-phosphocholine (DOPC).

22. The method of claim 15, wherein the lipid bilayer comprises 1,2-bis[10-(2',4'-hexadienoyloxy) decanoyl]-sn-glycero-3-phosphocholine (bis-SorbPC).

23. A method of forming a lipid bilayer on the surfaces of one or more microchannels;

providing a microfluidic device having one or more microchannels including a constriction region having a width within the range of about 4 μm to about 10 μm, the one or more microchannels comprising one or more hydrophilic surfaces; and flowing lipid bicelles into the one or more microchannels formed using a long-chain phospholipid component and a short-chain phospholipid component, wherein the lipid bicelles naturally interact with the one or more hydrophilic surfaces of the one or more microchannels and rupture liberating the short-chain phospholipid component to form a lipid bilayer comprising the long-chain phospholipid component that conformally coats the one or more hydrophilic surfaces.

24. The method of claim 23, wherein the long-chain phospholipid component comprises phospholipid 1,2-dioleoyl-sn-glycero-3-phosphocholine and the short-chain phospholipid component comprises 1,2-dihexanoyl-sn-glycero-3-phosphocholine (DHCP).

25. The method of claim 23, wherein the lipid bilayer comprising the long-chain phospholipid component conformally coats the constriction region.

* * * * *